(12) United States Patent
Gupta et al.

(10) Patent No.: US 7,655,678 B2
(45) Date of Patent: Feb. 2, 2010

(54) PHARMACEUTICAL COMPOSITION FOR THE MANAGEMENT OF TUMORS

(75) Inventors: Krishna Prabha Gupta, Lucknow (IN); Jaya Singh, Lucknow (IN)

(73) Assignee: Council of Scientfic & Industrial Research, New Delhi (IN)

(*) Notice: Subject to any disclaimer, the term of this patent is extended or adjusted under 35 U.S.C. 154(b) by 126 days.

(21) Appl. No.: 11/288,968

(22) Filed: Nov. 29, 2005

(65) Prior Publication Data

US 2006/0281793 A1 Dec. 14, 2006

(30) Foreign Application Priority Data

Dec. 10, 2004 (IN) .................. 2460/DEL/2004

(51) Int. Cl.
*A61K 31/455* (2006.01)
*A61K 31/19* (2006.01)
(52) U.S. Cl. ..................... 514/356; 514/557
(58) Field of Classification Search ......... 514/356, 514/557
See application file for complete search history.

(56) References Cited

U.S. PATENT DOCUMENTS 5,053,396 A * 10/1991 Blass .................. 514/45
6,718,910 B1 * 4/2004 Koyama et al. ......... 119/51.01

FOREIGN PATENT DOCUMENTS

WO 9511699 * 5/1995

OTHER PUBLICATIONS

Hanausek et al, Integrative Cancer Therapies, vol. 2, No. 2, 139-144 (2003).*
Alternate medicine, 2002, 1-5 and Hoskin et al. Br-J-Cancer. 1997; 76(2): Abstract only.*
Hoskin et al. Br-J-Cancer. 1997; 76(2): Abstract.*
Moss Expert Guidance for Crucial Decisions, 1998, 1-3.*
Kamat et al. Redox-Rep. 1999; 1 page only.*
Ludwig et al. Cancer research, 50 2470-2475, 1990.*
Moss "New Developments in Complementary Cancer Treatment" 2001, 1-10.*

* cited by examiner

*Primary Examiner*—Michael G Hartley
*Assistant Examiner*—Shirley V Gembeh
(74) *Attorney, Agent, or Firm*—Meyertons, Hood, Kivlin, Kowert & Goetzel, P.C.; Eric B. Meyertons

(57) ABSTRACT

The present invention relates to the effect of naturally occurring compounds on tumor development. As an example of proof, we used low; non-toxic doses of three compound e.g. Calcium D-glucarate, a naturally occurring $Ca^{++}$ salt of D-glucaric acid; Nicotinamide (NA), a naturally occurring vitamin and butyric acid (BA), a naturally occurring saturated short chain fatty acid. 7,12 dimethylbenzanthracene (DMBA), which is a very potent skin carcinogen and is an environmental pollutant, was used for skin tumor development. Experiment was performed up to 30 weeks. All the above-mentioned compounds were used either alone or concomitantly any two or all the three. In the positive control group 100% tumorigenesis was attained in 28 weeks, use of single compound led to the inhibition of DMBA induced tumorigenesis between 33 to 47%, use of two compounds resulted in the 73 to 80% reduction in tumorigenesis but the concomitant use of three compounds resulted into 100% inhibition of tumor development at the end of 30 weeks. This led us to conclude that the concomitant use of Cag, NA and BA in combination of two is useful for preventing skin tumor development for a sort or long period of time. But the concomitant use of all the three compounds, as described, exhibited the perfect synergistic effect in preventing the tumor development completely. This strategy should be equally effective in the management of benign and possibly malignant tumor in any organ caused by any mean.

5 Claims, No Drawings

PHARMACEUTICAL COMPOSITION FOR THE MANAGEMENT OF TUMORS

FIELD OF INVENTION

The present invention relates to a pharmaceutical composition for the management of tumors. More particularly, the present invention relates to concomitant use of naturally occurring compounds for the management of tumors. In general, the present invention relates to the complete protection of 7,12-dimethylbenz anthracene [hereafter DMBA] induced mouse tumor development specifically in skin, at least up to 30 weeks with the topical application of three naturally occurring compounds namely Calcium-D-Glucarate, Nicotinamide and Butyric acid, concomitantly.

BACKGROUND OF INVENTION

The incidence of skin cancer continues to increase globally and western countries are on the higher risk. Environmental pollutants, industrial chemicals, cosmetics, solar ultraviolet (UV) radiation etc. have been implicated as its major cause of skin cancer. This adverse effect has become a major human health concern.

Tumor development does not involve just one event. It is an outcome of the cumulative/additive/synergistic effects of different metabolic/molecular/biochemical events. There are different mechanisms responsible for the tumor development. Hence, use of one agent is not effective in controlling the tumor development and its management. Because one agent can not modulate all the processes going on for the tumor development, therefore there is a need to develop novel strategies to reduce the occurrence of cancer in general. This can be best accomplished by the use of the combination of drugs/agents/compounds of different mode of action. Tumor development can be prevented or delayed in the high-risk populations using dietary or chemical interventions. Hence, for the therapeutic/preventive strategies we have developed a strategy that involves the use of combination of compounds of different mode of action using mouse model of skin tumor development. We have used naturally occurring non-toxic compounds for this study. Agents under study include: Calcium glucarate—a naturally occurring fruit constituent which has potent detoxification activity through glucuronidation mechanism; Nicotinamide—a naturally occurring vitamin involved in different metabolic pathways and Butyric acid—a naturally occurring—non toxic short chain fatty acid which is a potent inhibitor of histone deacetylase activity. We performed a series of experiments to suggest that concomitant application of these three compounds under the experimental conditions gives much better effects as compared to that of the single compound or combination of two. Since our study involves the use of non toxic, naturally occurring compounds, we suggest that this combination strategy could be applied for the management of tumor development effectively. This could be cost effective too.

The present invention is directed to the prevention of skin tumor development for which no fully satisfactory/safer compound(s) is/are currently available. Skin cancer is a form of malignant neoplasm in the human population and accounts for about fifty percent of all cancers in western population. Skin has great importance as an organ that interfaces with the external environment and constitutes a barrier and transition zone between the external and internal milieu. The main causes of skin cancer are repeated sunburn, overexposure to the ultraviolet rays of the sun and environmental pollutants like polycyclic hydrocarbons mainly coal tar, 7,12-dimethylbenz (a) anthracene, Benzo (a) pyrene, Benzo (e) pyrene and a mixture of 4-6 benzene ring compounds. Reference may be made to William M. B. et al, 1997, (1).

Over the last 3-5 decades, the treatment of cancer has relied primarily on the use of various forms of cytotoxic chemicals in chemotherapy and radiation therapy. These interventions have had profound positive results in cases of many hematologic malignancies and a few solid tumors. In Case of skin cancer mostly the treatments include surgical removal, electrosurgery/cauterization of small tumors and cryosurgery. Radiotherapy is also used either in addition to surgery or alone. For benign skin tumors surgical removal is the most common treatment (88%) but for malignant types there is no such effective treatment as yet. If left untreated it can invade and metastasize in different organs of the body especially the liver, lungs, bones and is then fatal. Unfortunately most drugs used in cancer chemotherapy are highly cytotoxic to normal tissues. References may be made to Verma A. K, 2003 (2) where retinoic acid, a metabolite of vitamin A reduced the development of mouse skin papillomas to some extent but at higher concentrations it was cytotoxic. To prevent the occurrence of skin cancer, the use of sunscreen and wearing protective clothing's are recommended and are in practice. These are important strategies but unfortunately these effects are only partially effective. Thus the development of novel strategies to reduce the occurrence of skin cancer is highly desirable goal. One good approach is chemoprevention, where naturally occurring agents or synthetic compounds are used to prevent the occurrence and subsequent development of cancer. Cancer chemoprevention is a powerful strategy for the chemoprevention of cancer and combinatorial strategies provide dramatic improvements over monotherapeutic regimens. This principle has been successfully applied to the treatment of leukemia's (3), acquired immunodeficiency syndrome (AIDS) (4) and tuberculosis (5). Reference may be made to Alam et al, 2002 (6) Where chemopreventive potential of *Vitis vinifera* against 12-O-tetradecanoyl phorbol-13-acetate (TPA)-mediated tumor promotion in 7,12-dimethylbenz anthracene (DMBA) initiated mouse skin following two-stage initiation promotion protocol was assessed. Treatment with *vitis vinifera* 1 h prior to each application of TPA resulted in partial protection against tumorigenesis in a dose dependent manner.

Reference may be made to Singh et al, 1998, (7) where inhibitory potential of *Momordica charantia* (Bitter gourd) peel, pulp, seed and whole fruit extract on mouse skin papillomagenesis was assessed. Topical application of *Momordica* whole fruit extract (100 microg/animal per day) during the pre-initiation stage (1 week before and 2 weeks after initiation) by 7,12-dimethylbenzantracene (DMBA) and/or during the tumor promotion stage reduced the (i) tumor burden, (ii) cumulative number of papillomas and (iii) percent incidence of mice bearing papillomas. Reference may be made to Bala M et al, 2002, (8). In an in-vivo experiment, topical application of 7-Isopentenyloxucoumarin suppressed skin tumor formation induced by 12-O-tetradecanoylphorbol-13-acetate (TPA) in 7,12-dimethylbenzanthracene(DMBA) initiated mice. Reference may be made to Dwivedi C. and Zhang, Y, 1999, (9) where they have used topical application of sandalwood oil on DMBA initiated and TPA promoted mouse skin and they observed 67% decrease in papilloma incidence 20 weeks after promotion but there was no effect on papillomas formed by complete carcinogenesis.

Chemoprevention by a single agent is limited by both toxicity and potency. Thus chemoprevention-using combination of compounds with different modes of action is an exciting new field. Several such clinical trials are in progress. Reference may be made to Fisher, M. et al, 2003, (10). The cyclooxygenase-2(COX-2) inhibitor Celecoxib and the ornithine decarboxylase (ODC) inhibitor difluoromethylornithine (DFMO) were used in combination to prevent skin tumor development throughout the course of UV irradiation in SKF hairless mice. The group receiving the combination of Celecoxib and DFMO showed the greatest regression, with 89% reduction in number of tumors as compared with the control group. Drawbacks of the referred work are that they have used synthetic compounds which are cytotoxic in long term use and the combination of these two compounds didn't give 100% protection from skin tumors.

Reference may be made to Dwivedi et al., 1992, (11). The effects of diallyl sulfide and diallyl disulfide, oil soluble constituents of garlic and onion, on 7,12-dimethylbenz (a) anthracene induced and 12-O-tetradecanoyl phorbol-13-acetate promoted skin tumor formation were examined in SENCAR mice. Topical application of diallyl sulfide or diallyl disulfide significantly inhibited skin papilloma formation from the ninth week of promotion and significantly increased the rate of survival in the murine model. The apparent drawback of the referred study is the lack of 100% protection from skin papillomas even after using natural compounds.

Reference may be made to Slaga, T. J., 1984, (12). Skin tumor promotion was inhibited by a combination of the inhibitors of stage I and II. Skin carcinogenesis was counteracted by the combination of low and nontoxic doses of BHA, TPCK, DFMO and vitamin E. Here again a drawback of the referred work is that in spite of using a combination of inhibitors of tumor initiation and promotion 100% protection was not observed.

Reference may be made to Afaq, et al, 2002, (13). Here, botanical antioxidants for chemoprevention of photocarcinogenesis of skin cancer were used. The use of botanical antioxidants in combination with the use of sunscreens and educational efforts to avoid excessive sun exposure, is an effective strategy for reduction in incidence of skin cancer and other UV-mediated damage in humans. The drawback of the refereed work is that this strategy is only partially effective for the prevention of skin tumors.

The ideal chemopreventive agent for prevention of skin cancer must possesses none or minimal toxicity. In view of this, we have taken three different naturally compounds with different modes of action. These compounds have been reported to be safe with no reported toxicity.

Since we are studying the protection of skin tumors, the ideal route of application should be topical so that the drug can be applied directly to the affected site. We have given all the treatments topically in the interscapular region of the back of the mouse. All the three compounds, namely, Calcium D-glucarate, Nicotinamide and Butyric acid used were pure and procured from the commercial sources. They have well defined molecular structures and their modes of actions are also reported.

We propose the use of compounds of different activity in combination for the prevention. Here we have used compounds with different modes of action. When these compounds were used alone, some protection of tumorigenesis was observed but when all the three compounds were used concomitantly, no tumor development was observed.

Reference may be made to Hecht, et al, 2002, (14) where in they have used N-acetyl-S-(N-2-phenethylcarbaloyl)-L-cysteine (PEITC-NAC) and myoinositol in combination for lung tumor prevention in A/J mice by oral supplementation up to 27 weeks. When administered together PEITC-NAC and myoinositol reduced lung tumor multiplicity by 64.7%. The drawback of the referred work is that they have used synthetic compounds, which produces cytotoxicity when used for longer period of time. Another drawback is that they have not observed complete protection of lung tumorigenesis.

Reference may be made to Kitamura et al, 2003, (15). Here they have investigated the combined effect of EP-1 and EP-4 antagonists on spontaneous polyp formation in APC 1309 mice in order to determine the contribution of receptor to intestinal tumorigenesis. There was 56% reduction in colon carcinogenesis with this treatment. The drawback of the referred work is that in spite of using such a targeted approach, workers didn't observe 100% protection of intestinal carcinogenesis.

Reference may be made to Torrence et al, 2000, (16). Sulindac, a prototypical non-steroidal anti-inflammatory drug and EKI-785, an irreversible inhibitor of the epidermal growth factor receptor kinase were used in combination for chemoprevention of intestinal neoplasia. Although, in combination Sulindac and EKI-785 reduced intestinal polyp incidence by 95-97%, the significant toxicity associated with long term NSAID use can not be avoided (17). Such toxicity severely compromises the overall value of NSAID-mediated chemoprevention in high-risk individuals.

We have used three different naturally occurring compounds as detailed below. a) Calcium-D-Glucarate. Calcium D-glucarate is calcium salt of D-glucaric acid, a substance produced in small amounts by mammals, including humans. Glucaric acid is also found in many fruits and vegetables with the highest concentrations being found in oranges, apples, grapefruits and cruciferous vegetables (18). Calcium D-glucarate's detoxifying and anticarcinogenic properties are attributed to its ability to increase glucuronidation and excretion of potentially toxic compounds. During phase II detoxification, chemical carcinogens, steroid hormones and other lipid-soluble toxins are conjugated with glucuronic acid in the liver (glucuronidation), and excreted through the biliary tract. b-glucuronidase is capable of conjugating these potential toxins, making it possible for them to be reabsorbed rather than excreted. D-glucaro-1,4 lactone is the metabolite that has been shown to inhibit b-glucuronidase activity thereby increasing excretion of conjugated xenobiotic compounds and decreasing activity of harmful substances that are most active in their deconjugated state (19,20). Inhibition of B-glucuronidase ultimately results in potentially decreasing the risk of carcinogenesis (21). We have already reported the tumor inhibitory effects of calcium glucarate alone (22) and have also cited several reports therein with reference to the management of tumor by calcium glucarate.

b) Nicotinamide: Nicotinamide, the amide derivative of nicotinic acid has been classed as a food additive rather than a drug and therefore requires no formal safety evaluation (23). Nicotinamide is a specific inhibitor of ADP-ribose transferase (PARP)(24). The 50% inhibition concentration of nicotinamide for PARP is nearly 0.1 mM (25,26). Nicotinamide is an inhibitor of PARP, which is involved in base excision repair. Cells lacking PARP are much more fragile and undergo programmed cell death faster than parental cells due to accumulation of unrepaired DNA damage (because of absence of PARP). Cells with unrepaired DNA damage are unable to undergo cell cycle pathway and engage the apoptotic pathway to avoid transmission of damaged DNA to a new generation of cells. Thus nicotinamide induces apoptosis in initiated cells. We have already reported the tumor inhibitory effects of nicotinamide alone (27) and have also cited several reports therein with reference to the management of tumor by nicotinamide.

c) Butyric acid: Butyric acid is a short chain fatty acid, which is an inhibitor of histone deactylase activity (HDAC)

(28). Butyric acid has multiple effects on cultured mammalian cells that include inhibition of proliferation, induction of differentiation and induction or repression of gene expression. Inhibition of HDAC activity leads to hyperactylation and transcriptional activation of the p21 Waf1/Cip1 gene; p 21. Waf1/Cip 1 inhibits cyclin-dependent kinase-2 activity and thereby arrests cell cycling. Pending the cell background, the non-proliferating cells may enter differentiation or apoptotic pathways. We have already reported the tumor inhibitory effects of butyric acid alone (29) and have also cited several reports therein with reference to the management of tumor by butyric acid.

The main object of the present invention is to provide concomitant use of naturally occurring compounds to prevent skin tumor formation in mouse, which obviates the drawbacks as detailed above.

SUMMARY OF INVENTION

The overall objective of the present invention is, to provide a combination of compounds with different modes of action to prevent tumor development with specific reference to skin tissue. The present invention is superior over others as the route of application is topical and the compound is applied directly to the affected tissue.

One embodiment of the present invention is the concomitant use of non-toxic amounts of the following compounds in a pharmaceutically acceptable excipient:
1. Cag
NA
BA In another embodiment of the present invention, the following non-toxic doses of the compounds were used:
1. About 0.05 mg to about 20 mg Cag
2. About 0.05 mg to about 20 mg NA
3. About 25 umoles to about 500 umoles BA.
4. About 0.05 mg to about 20 mg Cag+ about 0.05 mg to about 20 mg NA
5. About 0.05 mg to about 20 mg Cag+ about 25 umoles to about 500 umoles BA.
6. About 0.05 mg to about 20 mg NA+ about 25 umoles to about 500 umoles BA.
7. About 0.05 mg to about 20 mg Cag+ about 0.05 mg to about 20 mg NA+ about 25 umoles to about 500 umoles BA.

In a preferred embodiment of the present invention, the following non-toxic doses of the compounds were used.
About 1 mg to about 15 mg Cag
2. About 1 mg to about 15 mg NA
About 50 umoles to about 400 umoles BA.
About 1 mg to about 15 mg Cag+ about 1 mg to about 15 mg NA
About 1 mg to about 15 mg Cag+ about 50 umoles to about 400 umoles BA.
About 1 mg to about 15 mg NA+ about 50 umoles to about 400 umoles BA.
About 1 mg to about 15 mg Cag+ about 1 mg to about 15 mg NA+ about 50 umoles to about 400 umoles BA.

In another preferred embodiment of the present invention, the following non-toxic doses of the components were used.
About 2 mg to about 10 mg Cag
About 2 mg to about 10 mg NA.
About 100 umoles to about 350 umoles BA.
About 2 mg to about 10 mg Cag+ about 2 mg to about 10 mg NA
About 2 mg to about 10 mg Cag+ about 100 umoles to about 350 umoles BA.
About 2 mg to about 10 mg NA+ about 100 umoles to about 350 umoles BA.
About 2 mg to about 10 mg Cag+ about 2 mg to about 10 mg NA+ about 100 umoles to about 350 umoles BA.

In still another embodiment of the present invention, the following non-toxic amounts of the components were used
About 3 mg to about 8 mg Cag
About 3 mg to about 8 mg NA.
About 150 umoles to about 300 umoles BA.
About 3 mg to about 8 mg Cag+ about 3 mg to about 8 mg NA
About 3 mg to about 8 mg Cag+ about 150 umoles to about 300 umoles BA.
About 3 mg to about 8 mg NA+ about 150 umoles to about 300 umoles BA
About 3 mg to about 8 mg Cag+ about 3 mg to about 8 mg NA+ about 150 umoles to about 300 umoles BA.

In yet another embodiment of the present invention, the following non-toxic amounts of the components were used.
About 4 mg to about 7 mg Cag
About 4 mg to about 7 mg NA.
About 175 umoles to about 250 umoles BA.
About 4 mg to about 7 mg Cag+ about 4 mg to about 7 mg NA
About 4 mg to about 7 mg Cag+ about 175 umoles to about 250 umoles BA.
About 4 mg to about 7 mg NA+ about 175 umoles to about 300 umoles BA
About 4 mg to about 7 mg Cag+ about 4 mg to about 7 mg NA+ about 175 umoles to about 300 umoles BA.

In a further embodiment of the present invention, the following non-toxic amounts of the components were used
About 6 mg Cag
About 6 mg NA.
About 200 umoles BA.
About 6 mg Cag+ about 6 mg NA.
About 6 mg Cag+ about 200 umoles BA.
About 6 mg NA+ about 200 umoles BA.
About 6 mg Cag+ about 6 mg NA+ about 200 umoles BA.

In another preferred embodiment of the present invention, the following non-toxic amounts of the components were used
6 mg Cag
6 mg NA.
200 umoles BA.
6 mg Cag+6 mg NA
6 mg Cag+200 umoles BA.
6 mg NA+200 umoles BA.
6 mg Cag+6 mg NA+200 umoles BA Accordingly the present invention provides a pharmaceutical composition for the management of tumors comprising calcium glucarate, nicotinamide and butyric acid in combination of either of two or all the three, for the best results, along with pharmaceutically acceptable excipients, diluents or carriers.

In an embodiment of the present invention, we have used low and non-toxic doses of Cag and NA to prevent skin tumor development.

In another embodiment of the present invention we have used low and non-toxic dosage of Cag and Butyric acid.

In yet another embodiment of the present invention we have used low and non-toxic dosage of NA and butyric acid.

In still another embodiment of the present invention we have used low and non-toxic dosage of Cag, NA and BA concomitantly on mouse skin.

Main Advantages of the Present Invention:
To reduce the occurrence of skin cancers, the use of sunscreens and wearing protective clothing are recommended and are in practice while in sun. These are important strategies but unfortunately these effects are only partially effective. Thus, the development of novel strategies to reduce the occurrence of skin cancer is highly desirable goal. One good approach is chemoprevention, where the use of naturally occurring agents or synthetic compounds is done to prevent the occurrence and subsequent development of cancer. The ideal chemopreventive agent which could be used for prevention of skin cancer must possesses none or minimal toxicity. We have also taken three different naturally occurring compounds with different modes of action. These compounds have been reported to be safe with no reported toxicity.

Since we are looking for a combination of drugs to prevent skin tumors the ideal route of application should be topical so that the drug can be applied directly to the exposed site. We have given all the treatments topically in the interscapular region of the back of the mouse. All the three compounds, namely, Calcium D-Glucarate, Nicotinamide and Butyric acid used were pure and procured from the commercial sources. They have well defined molecular structures and their modes of actions are also reported.

We propose the use of compounds of different activity in combination therapy. Here we have used compounds with different modes of action. When these compounds were used alone, some protection of tumorigenesis was observed but, when these compounds were used in combination of either of two, protection was significantly increased and in combination of all the three compounds there was complete protection of mouse skin tumor development.

Novelty of the present invention resides in the use of the 3 compounds in combination of either two for the better protection/management of tumor and further, use of all these three compounds for the complete protection of tumor development/management. To the best of our knowledge, this kind of study is not reported earlier. Skin carcinogenesis can be categorically defined in different stages that take place during the tumor development. Different pathways are involved in different stages. They are—tumor initiation, tumor promotion and alternatively complete carcinogenesis. We used Calcium glucarate that affects tumor initiation and by modulating different biochemical and molecular events. Nicotinamide and butyric acid inhibit tumor promotion by entirely different mechanisms and by inducing differentiation. Tumor development is a complex process that involves numerous known and unknown processes and should be checked at all the possible stages of its development. Thus prevention by a single compound doesn't lead to complete protection of tumor formation. Furthermore, skin carcinogenesis can be counteracted by a combination of low and nontoxic doses of Cag, Na and BA. Complete inhibition of tumor development by the use of compounds of different origin and mechanisms of action is the novelty of our study.

DETAILED DESCRIPTION OF THE INVENTION

We have used female Swiss albino mice from the inbred colony of Industrial Toxicology Research Center, Lucknow, India. The treatment schedule was followed as described earlier (22). Animals were shaved on the back (2×2 cm) in the interscapular region using surgical clippers. Only the animals in the resting phase of hair growth were selected for the study. For this chronic animal bioassay, we have taken 135 animals and divided them into 9 groups, consisting of 15 animals each. Group 1 served as negative control group where animals received acetone/DMSO only. For the entire study we have used 7,12-Dimethylbenz (a) anthracene (DMBA) as a skin carcinogen. DMBA was used at the dose of 200 µg/kg body wt in 0.1 ml acetone. In group 3, animals were treated with DMBA followed by concomitant application of Calcium D-glucarate (240 mg/kg body wt in 0.1 ml of DMSO). In group 4 animals were treated with DMBA followed by concomitant application of Nicotinamide (240 mg/kg body wt 0.1 ml of acetone). In group 5, animals were treated with DMBA followed by concomitant application of Butyric acid (8 mmoles in 0.1 ml of acetone). In group 6, animals were treated with DMBA followed by concomitant application of Calcium D-glucarate and Nicotinamide. In group 7, animals were treated with DMBA followed by a concomitant application of Calcium D-glucarate, Butyric acid. In group 8, animals were treated with DMBA followed by concomitant application of Nicotinamide and butyric acid. In group 9, animals were treated with DMBA followed by concomitant application of Calcium D-glucarate, Nicotinamide and Butyric acid. All the treatments were applied topically. We have always given the treatments in the order mentioned in experimental design. Animals were inspected regularly for tumor incidence, baldness, acne, poor health, sickness etc. Experiment was terminated after 30 weeks.

Experimental Design (15 Animals Each Group)

| Serial No. | Groups | Treatment | Route o Application | Treatment Schedule |
|---|---|---|---|---|
| 1. | Group1 (Negative control) | Acetone/ DMSO | Topical | Twice Weekly |
| 2. | Group 2 (Positive Control) | DMBA | " | " |
| 3. | Group 3 | DMBA + Cag | " | " |
| 4. | Group 4 | DMBA + NA | " | " |
| 5. | Group 5 | DMBA + BA | " | " |
| 6. | Group 6 | DMBA + Cag + NA | " | " |
| 7. | Group 7 | DMBA + Cag + BA | " | " |
| 8. | Group 8 | DMBA + NA + BA | " | " |
| 9. | Group 9 | DMBA + Cag + NA + BA | " | " |

Results

| Sl No. | Treatment | Onset of firs tumor [in weeks] | 100% tumorigenesis [in weeks] | Cumulative no. of tumor | No. of tumo bearing animal/Initial No. of animals |
|---|---|---|---|---|---|
| 1 | CONTROL | 0 | 0 | 0 | 0/15 |
| 2 | DMBA | 15 | 28 | 62 | 15/15 |
| 3 | DMBA + CaG | 18 | 0 | 12 | 10/15 |
| 4 | DMBA + NA | 21 | 0 | 09 | 08/15 |
| 5 | DMBA + BA | 12 | 0 | 18 | 10/15 |

-continued

| Sl No. | Treatment | Onset of firs tumor [in weeks] | 100% tumorigenesis [in weeks] | Cumulative no. of tumor | No. of tumo bearing animal/Initial No. of animals |
|---|---|---|---|---|---|
| 6 | DMBA + CaG + NA | 21 | 0 | 06 | 04/15 |
| 7 | DMBA + CaG + BA | 18 | 0 | 08 | 03/15 |
| 8 | DMBA + BA + NA | 18 | 0 | 07 | 03/15 |
| 9 | DMBA + CaG + N + BA | 0 | 0 | 0 | 0/15 |

Doses used:
DMBA: 200 ug/kg body wt
CALCIUM GLUCARATE [Cag]: 240 mg/kg body wt
NICOTINAMIDE [NA]: 240 mg/kg body wt
BUTYRIC ACID [BA]: 8 mmoles/kg body wt

REFERENCES

William M. B. et al, (1997) in carcinogenic polycyclic hydrocarbons, 12, 171-179.
Verma A. K (2003). J. Biol. Regul. Haemosta. 170, 9
3. Slack, J. L. 1999, The biology and treatment of acute progranulocytic leukemia. Curr. Opin. Oncol. 11, 9-13.
4. Johnson, S. C & Gerber, J. G. 2000, Advances in HIV/AIDS therapy. Adv. Intern. Med., 45, 1-40.
5. Badtian I & Colebunders, R. 1999, Treatment and prevention of multidrug resistant tuberculosis. Drugs, 58, 633-661.
6. Alam et al, Pharmacol. Res. (2002), 46 (6), 55-64.
7. Singh et al (1998) Toxicol. Lett, 8, 449-453.
8. Bala M et a 1 (2002) Biol. Pharm. Bull. 25, 244-246.
9. Dwivedi C. and Zhang, Y (1999) Eur. J. Cancer Prev., 8, 449-455
10. Fisher, M. et al. (2003) Carcinogenesis, 24, 945-952.
11. Dwivedi et al. (1992) Pharm. Res. 9, 1668-1672.
12. Slaga, T. J. (1984) Acta Pharmacol Toxicol (Copenh), 55 Suppl 2, 107-124
13. Afaq, et al (2002) Front Biosci. 7, 784-792
14. Hecht, et al (2002) Carcinogenesis, 23, 1455-1461
15. Kitamura et al. (2003) Cancer Sci, 94, 618-621
16. Torrence et al, (2000) Nat. Med., 6, 974-975.
17. Bjorkman, D. J. 1998, Current status of nonsteroidal anti-inflammatory drug(NSAID) use in the United States: risk factors and frequency complications. Am. J. Med. 105, 85-105.
18. Dwivedi, C., Heck, W. J., Downie, A. A. 1990, Effect of Calcium glucarate on beta-glucuronidase activity and glucarate content of certain vegetables and fruits. Biochem Med Metab Biol, 43, 83-92
19. Walaszek, Z., Hanauszek-Walaszek, M. 1988, D-glucaro 1,4 lactone: its excretion in the bile and urine and effects on biliary excretion of betaglucuronidase after oral administration in rats. Hepatology, 9, 552-556.
20. Walaszek Z., Szemraj J., Narog , M et al. 1997, Metabolism, uptake and excretion of a D glucaric acid salt and its potential use in cancer prevention. Cancer Detect Prev. 21, 178-190.
21. Selkirk, J K., Cohen, G. M., McLeod, M. C. 1980, Glucuronic acid conjugation in the metabolism of chemical carcinogens by rodent cells. Arch. Toxicol. 139, 171-178.
22. Jaya Singh and Krishna P. Gupta (2003) Biomed and Environ Sciences. 16 9-16
23. Knip, M., Douek, I. F, Moore., W. P., Gilmor, H. A., McLean, M. E., Bingley, P. J., Gale, E. A. 2000, European nicotinamide diabetes intervention trial group. Safety of high dose Nicotinamide: a review, Diabetologia, 43, 1337-1345.
24. Hageman, G. J., Stierum, R. H., Van Herwijnen M. H., Vander Veer M. S., Kleinjans, J. C, 1998, Nutr Cancer, 32, 11-20.
25. DeMurcia G., Mennisier-de-Murcia J. 1994, PolyADP-ribose)polymerase: a molecular nick sensor. Trends Biochem Sci. 19, 1721-1726.
Shall S. ad Rad Biol, 11, 1-69.
Krishna P. Gupta (1999) Biomed and Environ Sciences. 12, 177-187.
Davie, J. R. 2003, Inhibition of histone deactylase activity by butyrate. J Nutr. 133, 2485-2493.
Krishna P. Gupta and N. K. Mehrotra (1997) Biomed and Environ Sciences. 10, 436-441

We claim:

1. A pharmaceutical composition for the management of skin tumors comprising calcium glucarate, nicotinamide, and butyric acid in combination with pharmaceutically acceptable excipients, diluents or carriers.

2. A composition as claimed in claim 1, comprising about 0.05 mg to about 20 mg calcium glucarate, about 0.05 mg to about 20 mg nicotinamide and about 25 μmoles to about 500 μmoles butyric acid.

3. A composition as claimed in claim 1, comprising about 6.0 mg calcium glucarate, about 6.0 mg nicotinamide, and about 200 μmoles butyric acid.

4. A composition as claimed in claim 1, wherein the composition is administered topically.

5. A composition as claimed in claim 1, wherein the composition is in the form of a cream, a milk, a pomade, a salve, an impregnated pad, a gel, a spray, or a lotion.

* * * * *